United States Patent [19]
Thompson

[11] 3,951,602
[45] Apr. 20, 1976

[54] SPECTROPHOTOMETRIC FORMALDEHYDE-COPPER MONITOR

[75] Inventor: Douglas Stuart Thompson, Newark, Del.

[73] Assignee: E. I. Du Pont de Nemours and Company, Wilmington, Del.

[22] Filed: June 25, 1974

[21] Appl. No.: 482,880

[52] U.S. Cl............. 23/230 R; 23/253 R; 106/1
[51] Int. Cl.² .................................. G01N 21/28
[58] Field of Search ............ 23/230 R, 253 R; 117/130 E; 106/1; 427/437

[56] References Cited
UNITED STATES PATENTS
3,532,519  10/1970  Hirohata et al.............. 106/1

OTHER PUBLICATIONS
Chem. Abstr. Vol. 73: 90564w (1970).
Chem. Abstr., Vol. 67: 29019g (1967).
Chem. Abstr., Vol. 78: 31895k (1973).
*Metalloberflaeche–Angew. Electrochem.*, Vol. 26(9), pp. 334–337, (1972).

Primary Examiner—Morris O. Wolk
Assistant Examiner—Timothy W. Hagan

[57] ABSTRACT

In an apparatus comprising a spectrophotometer, an inspection cell, and an electroless copper plating bath containing copper ions and formaldehyde for measuring the copper ion concentration of the bath spectrophotometrically, the improvement which comprises method and apparatus for spectrophotometrically measuring the formaldehyde concentration of the bath. The improved apparatus includes a source of reagent reactive with formaldehyde and a reaction vessel, useful for reacting the reagent with formaldehyde to produce a reaction product photoindicative of formaldehyde concentration.

3 Claims, 5 Drawing Figures

SPECTROPHOTOMETRIC FORMALDEHYDE-COPPER MONITOR

BACKGROUND OF THE INVENTION

1. Field of the Invention

This invention relates to the measurement of the concentrations of copper ions and formaldehyde in an electroless copper plating bath. More specifically, it relates to the measurement of the formaldehyde concentration spectrophotometrically and the use of a reagent in the measurement procedure which is reactive with formaldehyde but is not reactive with other components of the bath.

2. Description of the Prior Art

Electroless copper plating processes have been widely used for plating a metal film onto non-conductive plastics and for making printed circuit boards. The process usually utilizes a bath consisting of a strongly basic aqueous solution of a copper salt such as copper sulfate, a complexing agent such as N,N,N,N-tetrakis(2-hydroxypropyl) ethylenediamine, and a reducing agent, such as formaldehyde. Experience has shown that in the bath the copper ion and formaldehyde concentrations should be held at a specific ratio for optimum plating rates, plating thickness and bath stability, and replenishment of the copper ions and formaldehyde should be based on separate measurements of the two concentrations. A desirable means for measuring the formaldehyde concentration would be with a spectrophotometer. Methods have been proposed for spectrophotometrically measuring the formaldehyde concentration in a solution by reacting a reagent and the formaldehyde to produce a reaction product whose concentration is measurable and indicative of the formaldehyde concentration. Most of these methods would prove unsuitable for measuring formaldehyde in an electroless copper plating bath because they use reagents which would produce a strong reaction and react not only with the formaldehyde but also with the other components in the bath with the result that the formaldehyde concentration measurement would be affected. Another method has been proposed in an article "The Colorimetric Estimation of Formaldehyde by Means of the Hantzsch Reaction", T. Nash, Biochemical Journal, 55, 416, London (1953), in which the reagent chosen reacts only with formaldehyde. However, this method has been suggested for use only to measure formaldehyde concentration in living bacterial suspensions and in a biological environment and has never been suggested for use in measuring formaldehyde concentration in an electroless copper plating bath.

SUMMARY OF THE INVENTION

The present invention provides a technique in which formaldehyde is measured spectrophotometrically using a reagent which is reactive only with formaldehyde and non-reactive with other components of the bath. The method and apparatus for making the formaldehyde measurement is a distinct improvement of a known method and apparatus for spectrophotometrically measuring copper ion concentration in an electroless copper plating bath. The known apparatus includes the electroless copper plating bath, a spectrophotometer and an inspection cell adjacent to the spectrophotometer and in communication with the bath for providing bath samples to the inspection cell where the concentration is measured. The improved method and apparatus for measurement of the formaldehyde concentration includes the addition of: (a) a source of reagent reactive with formaldehyde to produce a reaction product photoindicative of formaldehyde concentration; (b) a reaction vessel in communication with the source of reagent; (c) a valved conduit which delivers samples of the bath solution to the reaction vessel, and (d) a conduit for delivering the reaction product to the inspection cell.

The reagent in the above method and apparatus contains acetylacetone and an ammonium salt and may contain acetic acid.

DESCRIPTION OF THE PREFERRED EMBODIMENT

Figure 1:
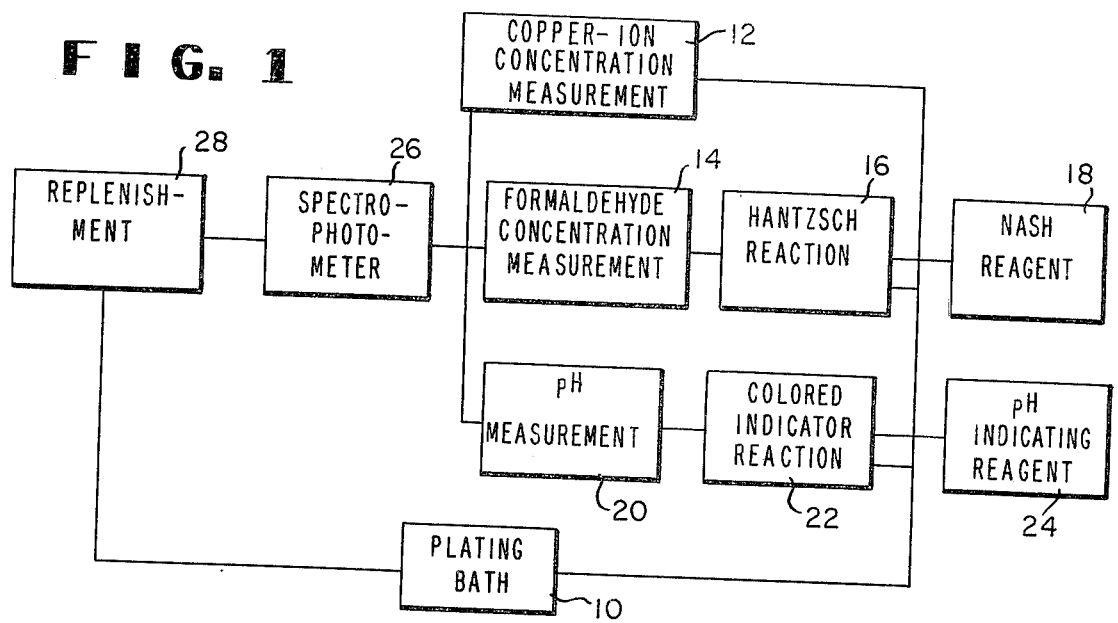
FIG. 1 is a diagrammatic representation of a system for measuring the concentrations of copper ions and formaldehyde in an electroless copper plating bath and replenishing the bath based on these measurements.

A system for continuously measuring copper ion concentration and periodically measuring formaldehyde concentration of an electroless copper plating bath and automatically replenishing the bath based on these measurements has been outlined in FIG. 1. The measurement of the pH of the bath and replenishment based on the measurement is optional.

The bath as shown in block 10 is an aqueous solution having the following composition:

| | Formula Weight | Mole/liter |
| --- | --- | --- |
| $CuSO_4 \cdot 5H_2O$ | 250 | 0.03–0.1 |
| HCHO | 30.03 | 0.031–0.052 |
| N,N,N,N-tetrakis(2-hydroxypropyl) ethylenediamine | 292 | 0.1–0.3 |
| NaOH | Adjusted to a pH of 12.7 | |

The copper ion concentration of the bath 10 is determined as indicated in block 12 by the spectrophotometer of block 26 which measures the amount of light absorbance by the bath at specific wavelengths. The copper ions are complexed with the complexing agent, N,N,N,N-tetrakis(2-hydroxypropyl)ethylenediamine, and have a maximum absorbance at a wavelength near 6900A at a pH of 12.7. The spectrophotometer of block 26 measures the amount of absorbance of light at this wavelength and compares it to the amount of absorbance of light at a reference wavelength of 4950A to indicate the concentration of copper ions. An electrical signal representative of the copper ion concentration is generated by the spectrophotometer and transmitted to an electronic control and pump of block 28 which replenishes the copper plating bath 10 with a proper amount of copper sulfate solution.

The formaldehyde concentration of the bath 10 is measured periodically as indicated in block 14 by the spectrophotometer of block 26. The formaldehyde in a bath sample from bath 10 is reacted with the reagent of block 18 in the Hantzsch reaction of block 16. The reagent of block 18 is called a Nash reagent and is described along with the Hantzsch reaction in the article by T. Nash referred to previously. The reagent is composed of the following components per 1000 ml. of solution: 2 ml acetylacetone, 150 grams ammonium acetate or ammonium salt, 2 ml acetic acid, with the remainder of the 1000 ml. solution being deionized water. In the reaction all of the formaldehyde in the bath sample is reacted to form a reaction product, diacetyldihydrolutidine, which has a maximum absorbance at 4150A. The absorbance at this wavelength is compared with the absorbance at a reference wavelength of 4950A to indicate the concentration of the reaction product and the formaldehyde. The spectrophotometer of block 26 in response to the formaldehyde concentration measurement generates an electrical signal representative of the formaldehyde concentration and transmits it to the electronic control and pump of block 28 which replenishes the bath with the proper amount of formaldehyde.

The measurement of the pH of bath 10 is optional and is done periodically as shown in block 20 by the spectrophotometer of block 26. To accomplish the measurement, a bath sample from bath 10 is reacted with the pH indicating reagent of block 24, Alizarin Yellow R, to give the rection product of block 22, which contains basic and acidic colored forms of Alizarin Yellow R. The concentration of the basic form increases as the pH in the bath sample increases, thus giving a measurement of pH. To obtain the numerical value of the pH, the absorbance of the basic form at 4950A is compared with the absorbance at a reference point at which the absorbance does not vary with pH. The reference point is at 4150A and occurs where the absorbance curves of the basic and acidic forms intersect, called an isobestic point. The absorbance curves for the basic and acidic forms show their light absorbance characteristics across the light wavelength spectrum. The spectrophotometer of block 26 in response to the pH measurement generates an electrical signal representative of the pH and transmits it to the electronic control and pump of block 28 which replenishes bath 10 with alkali hydroxide solution, as required, to adjust the pH.

Figure 2:
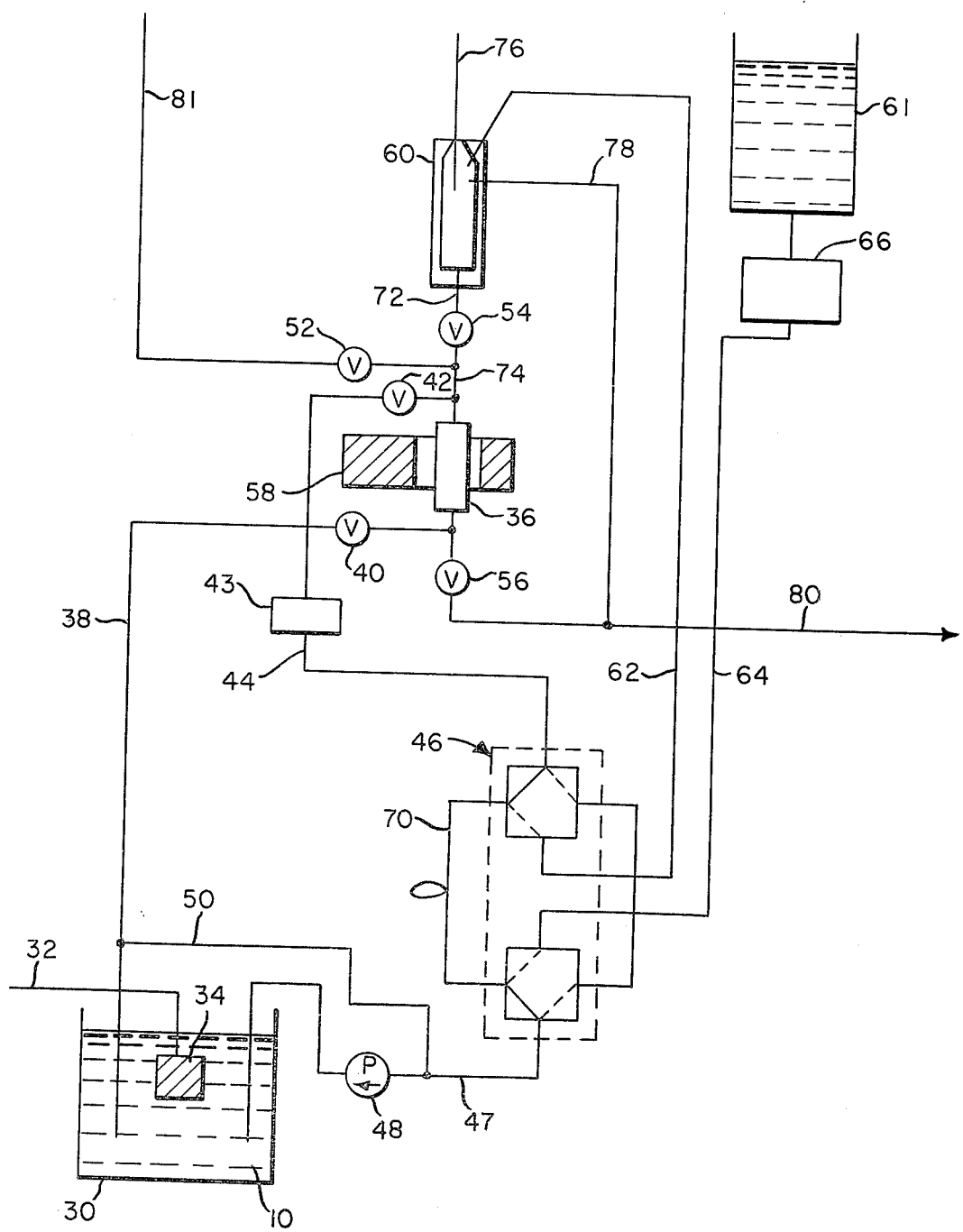
FIG. 2 is a schematic of apparatus for measuring the concentrations of copper ions and formaldehyde as outlined in FIG. 1.

FIG. 2 illustrates the apparatus represented in blocks 12, 14, 16, 18 and 26 of FIG. 1 for spectrophotometrically measuring the concentrations of copper ions and formaldehyde in bath 10. A vessel 30 contains the electroless copper plating bath 10 and has a support 32 holding a plastic sample 34 immersed in the bath to be copper plated. The bath is delivered to an inspection cell 36 through a conduit 38 and a valve 40 and is returned to vessel 30 through a valve 42, a bath cooler 43, a conduit 44, a formaldehyde sample valve 46, a conduit 47 and a pump 48. A bubble eliminator conduit 50 is provided from conduit 47 at the end of the pump 48 to conduit 38. Valves 40, 42, 52, 54, 56 are standard two-way valves such as those manufactured by the Fluorocarbon Co., Model DV2-224 and sample valve 46 is a Model SVA060 Special Sample Injection valve manufactured by Altex Scientific Inc. The valves are switched automatically in the proper time sequence by a sequencer (not shown) which may be any one of many commercially available. The inspection cell 36 is a polytetrafluoroethylene block with a longitudinal bore through which samples, which enter from bath 10 through conduit 38 and valve 40, pass for measurement. The block has two quartz plates adjacent to the longitudinal bore which allow for inspection of the samples by spectrophotometer 58, a Du Pont Model 400, which is located adjacent to both quartz plates of inspection cell 36. The spectrophotometer 58 measures the absorbance of the bath at the desired wavelength and generates an electrical signal representative of either copper ion or formaldehyde concentration which is sent to the electronic control and pump described in connection with block 28 of FIG. 1.

A reaction vessel 60 is connected to a vessel 61 containing the Nash reagent through a conduit 62, formaldehyde sample valve 46, a conduit 64, and a heater 66. Formaldehyde sample valve 46 contains a sample loop 70 which normally contains a fixed volume bath sample. When formaldehyde sample valve 46 is switched to the position shown in FIG. 4, both Nash reagent from vessel 61, which is being heated in heater 66, and the fixed volume bath sample from sample loop 70 drain into reaction vessel 60. The latter reaction vessel 60 is connected to inspection cell 36 through valve 54 and conduits 72, 74, which allow the contents of reaction vessel 60 to drain into inspection cell 36 where the spectrophotometric measurements are made. A cut-off probe 76 extends into reaction vessel 60 to provide an indication when the latter is filled to the proper level. Should probe 76 fail, an overflow conduit 78 drains any excess into drain 80. A source of flush water 81 is connected to inspection cell 36 through valve 52 and to drain 80 through valve 56.

Figure 3:
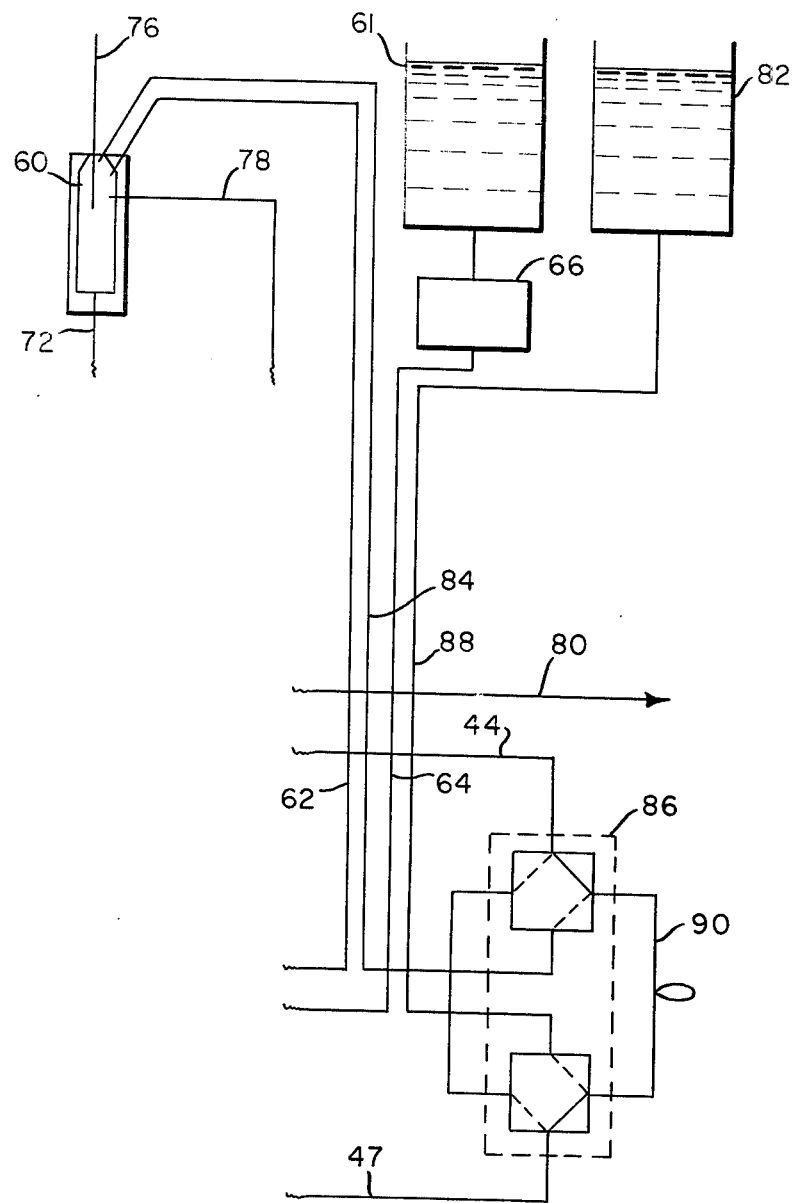
FIG. 3 is a schematic of optional apparatus for measuring the pH which is added to the apparatus of FIG. 2.

FIG. 3 shows optional apparatus that may be added to the apparatus shown in FIG. 2 for making pH measurements. A vessel 82 containing a pH indicated reagent Alizarin Yellow R is connected to reaction vessel 60 through conduit 84, pH sample valve 86 and conduit 88. pH sample valve 86 contains a sample loop 90 which normally contains a fixed volume bath sample. When pH sample valve 86 is switched to the position shown in FIG. 5, both Alizarin Yellow R from vessel 82 and the fixed volume bath sample from sample loop 90 drain into reaction vessel 60. Measurement of the pH is made in essentially the same manner as the formaldehyde is measured.

Figure 4:
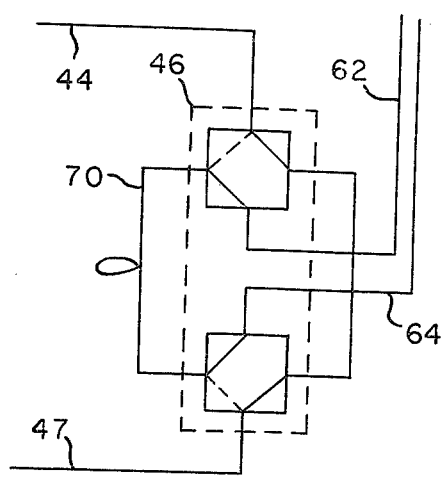
FIG. 4 is a schematic of the formaldehyde sample valve of FIG. 2 showing the paths of flow of fluid for the valve when switched to its alternative position.
Figure 5:
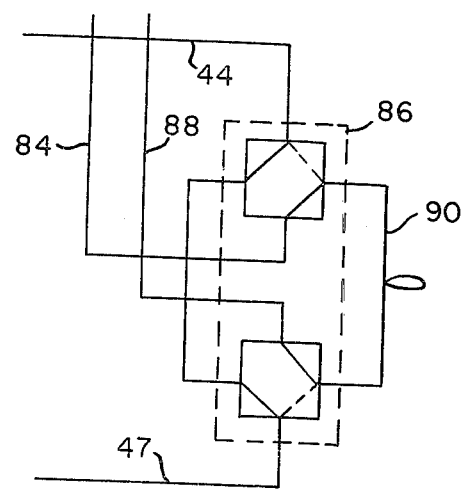
FIG. 5 is a schematic of the pH sample valve of FIG. 3 showing the paths of flow of fluid for the valve when switched to its alternative position.

FIG. 4 illustrates the flow of fluid in formaldehyde sample valve 46 when the valve is switched to its alternative position to allow Nash reagent to flow through sample loop 70 in preparation for the formaldehyde concentration measurement. Similarly, FIG. 5 shows the flow of fluid in pH sample valve 86 when the valve is switched to its alternative position to allow pH indicating reagent to flow through sample loop 90 in preparation for the pH measurement.

In operation, bath 10 from vessel 30 is continuously drawn by pump 48, through conduit 38 and valve 40 to inspection cell 36 where spectrophotometer 58 measures the copper ion concentration. Bath 10 returns to vessel 30 through valve 42, bath cooler 43, conduit 44, formaldehyde sample valve 46 in the position shown in FIG. 2, conduit 47 and pump 48. The spectrophotometer generates an electrical signal which, as described in connection with block 28 of FIG. 1, is transmitted to an electronic control and pump which replenishes copper sulfate to the bath. Valves 52, 54 and 56 are closed during the continuous measurement.

While the measurement of copper ion concentration is occurring, the system is preparing for the formaldehyde concentration measurement. Nash reagent from vessel 61 is warmed by heater 66 to 80°-90°C., preferably 85°C. Formaldehyde sample valve 46 is switched to the position shown in FIG. 4 which provides a path for Nash reagent from heater 66 flowing through conduit 64, to flow through formaldehyde sample valve 46 and sweep the fixed volume sample of bath from sample loop 70 through conduit 62 into reaction vessel 60. In addition, the latter sample valve provides a path for bath 10 to continue circulating along the same route followed during the copper ion concentration measurement as previously described. The Nash reagent continues to flow until it dilutes the bath sample to approximately a 50:1 volume ratio at which time cut off probe 76 senses the level of the solution and switches formaldehyde sample valve 46 back to the position shown in FIG. 2 to cut off the flow of the Nash reagent. The Hantzsch reaction begins and is 95% complete in about 4-5 minutes, however, it is allowed to continue for 10-15 minutes. When the reaction time is complete, valves 40, 42 are closed along with valve 54 and valves 52, 56 are opened up to allow inspection cell 36 to be flushed with flush water 81. After flushing, valve 52 is closed to shut off the flush water and valve 54 is opened, allowing the Hantzsch reaction product to flow into inspection cell 36. The initial surge of reaction product flows through inspection cell 36, flushes it and is wasted to drain 80. Valve 56 is then closed and a sample of the reaction product is trapped in inspection cell 36 where spectrophotometer 58 measures the absorbance of the reaction product to give an indication of formaldehyde concentration. The use of the Nash reagent permits the spectrophotometric measurement to be made from a reaction product containing only the formaldehyde component of the bath and avoids the problem of attempting to make the measurement from a reaction product containing other components of the bath. The spectrophotometer 58 generates an electrical signal which is transmitted to the electronic control and pump described in connection with block 28 of FIG. 1 to replenish the proper amount of formaldehyde to bath 10. Valves 54 and 56 are then opened to allow the sample cell and reaction vessel to drain. It has been found that measurement of formaldehyde concentration at 15 minute intervals is sufficient to keep the bath adequately replenished.

If the pH measurement is desired and the necessary apparatus is added as shown in FIG. 3, the measurement will occur at approximately 5 minute intervals and be done in essentially the same manner as the formaldehyde measurement. Since both the formaldehyde measurement and pH measurement require the use of reaction vessel 60, the two measurements cannot occur simultaneously and the reaction time for the formaldehyde must be shortened by about 5 minutes to allow for the pH measurement. While the continuous copper ion measurement is being made, pH sample valve 86 is switched to the position shown in FIG. 5 which allows bath 10 to continue circulating along the path followed during the copper ion concentration measurement as previously described and provides a path for the pH indicating reagent, Alizarin Yellow R, from vessel 82 flowing through conduit 88 to flow through pH sample valve 86 and sweep the fixed volume sample of bath from sample loop 90 through conduit 84 into reaction vessel 60. The pH indicating reagent continues to flow until it dilutes the bath sample to a 50:1 volume ratio at which time the cut off probe 76 senses the level of the solution and switches pH sample valve 86 back to the position shown in FIG. 3 to cut off the flow of the reagent. The reaction takes place rapidly. Then as shown in FIG. 2 valves 40, 42 are closed along with valve 54 and valve 52, 56 are opened to flush the sample cell. Valve 52 is then closed, shutting off the flush water, and valve 54 is opened, which allows the reaction product to drain into sample cell 36. The first portion of the reaction product flows through the inspection cell 36, flushes it, and is wasted to drain 80. Valve 56 is then closed and spectrophotometer 58 measures the concentration of the basic form of Alizarin Yellow R to give an indication of the pH. The spectrophotometer 58 generates an electrical signal which is transmitted to the electronic control and pump described in connection with block 28 of FIG. 1 to replenish the proper amount of sodium hydroxide to bath 10. Valve 56 is opened to allow the inspection cell 36 and reaction vessel 60 to drain. Valve 54 is then closed and valve 52 is opened along with valve 56 to allow sample cell 28 to be flushed.

The present invention is described in the preferred embodiments but it may be clear to those skilled in the art that modification and variation of this invention are possible within the teaching of this disclosure. All such modifications and variations are intended to be within the scope of the appended claims.

I claim:

1. In a method for the spectrophotometric measurement of the concentration of copper ion in an electroless copper plating bath containing copper ions and formaldehyde, the improvement which comprises:
   reacting a reagent containing acetylacetone and ammonium salt with said formaldehyde to produce a reaction product photoindicative of formaldehyde concentration in said bath, and
   spectrophotometrically measuring said reaction product to indicate said formaldehyde concentration.

2. The improvement as claimed in claim 1 wherein the reagent is further comprised of acetic acid.

3. In an apparatus including an electroless copper plating bath containing copper ions and formaldehyde, a spectrophotometer, and an inspection cell adjacent to the spectrophotometer and in communication with said bath for the determination of copper ion concentration in samples from the bath, the improvement comprising:
   a source of reagent reactive with said formaldehyde to produce a reaction product photoindicative of said formaldehyde concentration;
   a reaction vessel communicating with said source;
   means for delivering samples of said bath solution to said reaction vessel; and
   means for delivery of said reaction product to said inspection cell.

* * * * *